United States Patent
Oeltgen et al.

(10) Patent No.: US 6,544,950 B1
(45) Date of Patent: Apr. 8, 2003

(54) SEVENTEEN AMINO ACID PEPTIDE (PEPTIDE P) FOR TREATING ISCHEMIA AND REPERFUSION INJURY

(75) Inventors: Peter R. Oeltgen, Winchester, KY (US); Mark S. Kindy, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/003,328

(22) Filed: Dec. 6, 2001

(51) Int. Cl.[7] .................. A61K 38/00; A61K 38/04
(52) U.S. Cl. ................ 514/13; 514/2; 514/16; 530/300; 530/326
(58) Field of Search .............. 514/2, 13, 16; 530/300, 326

(56) References Cited

U.S. PATENT DOCUMENTS 6,294,519 B1    9/2001   Oeltgen et al.

OTHER PUBLICATIONS

Lazarus et al., "Frog Skin Opioid Peptides: A Case for Environmental Mimicry", Environmental Health Perspectives, vol. 102, No. 8, Aug. 1994, pp. 648–654.

*Primary Examiner*—Brenda Brumback
*Assistant Examiner*—B. Dell Chism
(74) *Attorney, Agent, or Firm*—McDermott, Will & Emery

(57) ABSTRACT

Peptide P, having the amino acid sequence Tyr-D-Ala-Phe-Ala-Asp-Val-Ala-Ser-Thr-Ile-Gly-Asp-Phe-Phe-His-Ser-Ile-NH2, is useful to treat ischemia.

2 Claims, 1 Drawing Sheet

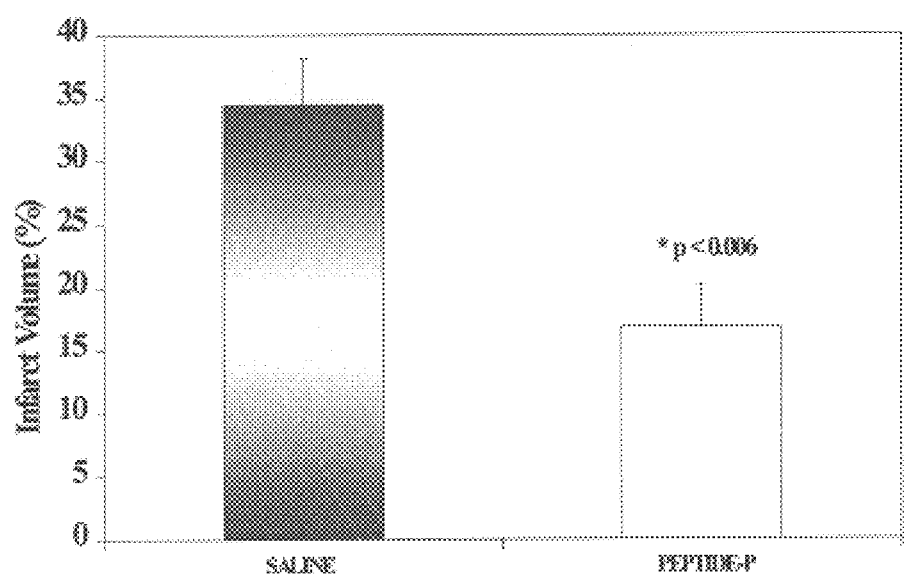

Fig. 1. Peptide-P at a concentration of 4 mg / Kg was injected (I. V.) 1 hr after occlusion of the external carotid artery (ECA). Controls were injected 100 µl physiological saline. Ischemic volume was assessed after 24 hrs of reperfusion. Treated animals showed a decrease in infarct volume, $p < 0.006$ compared to saline controls. Control had infarct size of $34.45 \pm 3.6\%$ and Peptide-P had $16.87 \pm 3.3\%$.

SEVENTEEN AMINO ACID PEPTIDE (PEPTIDE P) FOR TREATING ISCHEMIA AND REPERFUSION INJURY

FIELD OF THE INVENTION

The invention relates to the use of a novel seventeen amino acid peptide to treat cerebral ischemia and ischemic heart disease including reperfusion injury.

BACKGROUND

Tissues deprived of blood and oxygen undergo ischemic necrosis or infarction with possible irreversible organ damage. Cerebral ischemia results from decreased blood and oxygen flow implicating one or more of the blood vessels of the brain. In cerebral ischemia, the individual suffers a stroke with sudden development of a focal neurologic deficit and, in most cases, some degree of brain damage. The decreased blood flow may be due to, for example, an occlusion such as a thrombus or embolus, vessel rupture, sudden fall in blood pressure, change in the vessel lumen diameter due to atherosclerosis, trauma, aneurysm, developmental malformation, altered permeability of the vessel wall or increased viscosity or other quality of the blood. Decreased blood flow may also be due to failure of the systemic circulation and severe prolonged hypotension. Ischemic necrosis of the spinal cord may result in sensory or motor symptoms or both that can be referred to cervical, thoracic or lumbar levels of the spine. Ischemic heart disease results from an imbalance between myocardial oxygen supply and demand. In ischemic heart disease, the individual suffers angina pectoris, acute myocardial infarction or sudden death. The imbalance may be caused by, for example, atherosclerotic obstruction of one or more large coronary arteries, nonatheromatous coronary obstructive lesions such as embolism, coronary ostial stenosis associated with luetic aortitis, coronary artery spasm, congenital abnormalities of the coronary circulation, increased myocardial oxygen demands exceeding the normal supply capabilities as in severe myocardial hypertrophy, reduction in the oxygen carrying capacity of the blood such as n anemia, or as a consequence of inadequate cardiac perfusion pressure due to hypotension from any cause. U.S. Pat. No. 6,294,579 B1 discloses methods for treating ischemia by administering certain Deltorphin peptides. The publication by Lazarus et al., "Environmental Health Perspectives", Vol. 102, No. 4, pages 648–654 (1994), discloses naturally occurring opiod peptides.

Current treatments for ischemia encompass behavioral changes drug therapy, and/or surgical intervention. Drugs are frequently preferred before resorting to invasive procedures and to provide more immediate relief than long-term behavioral changes. Thus, there is a need for a therapeutic agent which can be useful in treating or preventing ischemia.

SUMMARY OF THE INVENTION

It is an object of the invention to provide a novel peptide and use of that peptide to treat ischemia.

The present invention meets the object by providing a novel seventeen amino acid peptide (Peptide P) which is useful for treating cerebral ischemia and ischemic heart disease. Also provided is a method of treating ischemia in a mammal comprised administering a pharmaceutically effective amount of Peptide P tc said mammal. The ischemic tissue may be brain, spinal cord or heart.

The present invention is also directed to a method of reducing the effect of an ischemic episode comprised of administering an effective amount of pharmaceutically effective amount of Peptide P to said mammal.

The present invention is also directed to a method of treating cerebral or spinal cord ischemia or ischemic heart disease in a mammal comprised of administering an effective amount of pharmaceutically effective amount of Peptide P to said mammal.

Preferably, Peptide P is administered as a pharmaceutical composition at a dosage in the range of about 0.5 mg/kg body weight to about 20 mg/kg body weight, or alternatively lower doses in the range of about 1 mg/kg body weight to about 1000 mg/kg body weight of the mammal. Preferably, the mammal is human.

BRIEF DESCRIPTION OF THE DRAWING

The sole FIGURE accompanying the application is a graph showing the effect of Peptide-P on infarct volume following cerebral ischemia.

DESCRIPTION OF THE INVENTION

Peptide P is a linear 17 amino acid peptide which has been synthesized on a commercial peptide synthesizer such as the type available from Applied Biosystem. Peptide P has the amino acid sequence Tyr-D-Ala-Phe-Ala-Asp-Val-Ala-Ser-Thr-Ile-Gly-Asp-Phe-Phe-His-Ser-Ile-NH2 and a MW of 1860.1 with alanine as D-isomer. The peptide P can be produced by a number of methods, such as by use of an automated peptide synthesizer, through recombinant molecular biology techniques, or isolated from a naturally occurring source.

Peptide P can be administered to ameliorate or inhibit damage caused by a stroke. A stroke is the acute neurologic injury caused by one of several pathologic processes involving the blood vessels of the brain. The pathologic process may be intrinsic to the vessel itself such as in arteriosclerosis, or may originate from a remote location such as an embolus, or may result from decreased perfusion or increased blood viscosity with inadequate cerebral blood flow, or may result from the rupture of a vessel in the subarachnoid space or intracerebral tissue.

The main causes of ischemic stroke are thrombosis, vasoconstriction and embolism. Diagnosis of a stroke can be readily made by one of ordinary skill in the art. Signs of stroke include paralysis, slurred speech, general confusion, impairment of gait, cortical sensory loss over toes, foot and leg and urinary incontinence, to name just a few. The diagnosis can be confirmed by cerebral angiography and by a computed axial tomography (CT) scan of the brain.

If a stroke occurs, Peptide P can be administered to limit injury to the brain. The ideal mode of administration is by intravenous (I.V.) or intraperitoneal (I.P.) injection at a dose of about 0.5–20 mg/kg, or alternatively, lower doses of about 1–1000 mg/kg. Peptide P can also be administered by subcutaneous or intraarterial injection into the carotid artery, or by direct injection into the brain, e.g., intracerebroventricular injection (ICV) for dispersion into other areas.

Very often a stroke is caused by a cerebral embolism, the likelihood of which can frequently be predicted. In these cases, the Peptide P can be administered prophylactically to prevent or lessen the amount of brain tissue injured during such an event. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of arteriosclerotic cardiovascular disease and myocardial infarction. Emboli formation and migration can occur as a result of arteriosclerotic cardiovascular disease and myocardial infarction. Emboli formation is also a definite risk for intracardiac surgery and prosthetic valve replacement. Heart bypass surgery and angioplasty can result in the formation of microemboli, which can migrate into the arteries of the brain and cause a series of occlusions in a number or arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli, which can occlude a major intracranial artery. Thus, when these disease states or surgical procedures are planned or are happening, Peptide P can be administered to prevent brain damage due to any resultant emboli and stroke.

Peptide P can be administered to ameliorate or prevent ischemic necrosis of the spinal cord. The ischemia may be caused by an endarteritis of surface arteries leading to thrombosis. Atherosclerotic thrombosis of the aorta or dissecting aortic aneurysms may cause infarction of the spinal cord (myelomalacia) by occluding nutrient arteries at cervical, thoracic or lumbar levels, as can paralysis during cardiac surgery requiring clamping of the aorta for more than 30 minutes and aortic arteriography. Infarctive or hemorrhagic vascular lesions of the spinal cord (hematomyelia) may result in the sudden onset of symptoms referable to sensory or motor or both spinal tract lesions.

Peptide P can also be administered to ameliorate or inhibit damage caused by ischemic heart disease. Ischemic heart disease is a general term for a spectrum of diseases of diverse etiology caused by an imbalance between oxygen supply and demand. The usual cause of the imbalance is atherosclerotic obstruction of large coronary arteries, leading to an absolute decrease in coronary artery blood flow. An imbalance may also result from nonatheromatous coronary obstructive lesions such as embolism, coronary ostial stenosis associated with luetic aortitis, coronary artery spasm, or very uncommonly an arteritis of the coronary vessels. The imbalance may also be due to congenital abnormalities of the coronary circulation, an increase in myocardial oxygen demands exceeding the supply capabilities in a normal coronary circulation, a diminished oxygen-carrying capacity of the blood such as in anemia or in the presence of carboxyhemoglobin (e.g., due to cigarette or cigar smoking), or as a consequence of inadequate perfusion pressure due to hypotension. When ischemic events are transient, they may be associated with angina pectoris: if prolonged, they can lead to myocardial necrosis and scarring with or without the clinical picture of acute myocardial infarction. Ischemic heart disease may be readily diagnosed by one skilled in the art. There may be predictive changes in the electrocardiogram, since ischemia alters electrical properties of the heart. Such changes include inversion of the T wave and displacement of the ST segment. Another important consequence of myocardial ischemia is electrical instability leading to ventricular tachycardia or ventricular fibrillation. Stress tests and coronary arteriography may also provide diagnostic information. These diagnostic test results may determine the need for Peptide P administration.

Since ischemic heart disease is usually asymptomatic until the extent of coronary artery blockage is well advanced, preventative measures to control risk factors and life style patterns associated with the disease are also recommended. In patients in the symptomatic phase of the disease, meticulous attention to life patterns or risk factors must be given in an attempt to promote lesion regression or at least prevent progression. Risk factors include a positive family history of ischemic heart disease, diabetes, hyperlipidemia, hypertension, obesity and cigarette smoking. Life patterns include sedentary lifestyle, psychosocial tension and certain personality traits.

Peptide P may be administered to asymptomatic individuals having one or more risk factors and/or life style patterns or to individuals already in the symptomatic phase of ischemic heart disease to reduce or prevent disease progression. Additionally, Peptide P may be administered to the following patients: those having careers that involve the safety of others (e.g., commercial airline pilots) and that present with questionable symptoms, suspicious or positive noninvasive test results, and in whom there are reasonable doubts about the state of the coronary arteries; males who are 45 or older and females who are 55 will undergo valve replacement and who may or may not have clinical evidence of myocardial ischemia; and those at high risk after myocardial infarction because of the recurrence of angina, heart failure, frequent ventricular premature contractions, or signs of ischemia in the stress test, to name just a few. Peptide P may be administered either separately or in combination with other cardiac drugs such as nitrates, beta-adrenergic blockers, calcium channel antagonists and/or aspirin and either separately or in combination with fibrinolytic drugs such as tissue plasminogen activator (tPA), streptokinase and urokinase. Use of Peptide P may prolong life and/or reduce or eliminate the need for invasive procedures such as coronary arteriography and coronary artery bypass grafting.

According to the present invention, Peptide P is administered to a mammal to treat cerebral or spinal cord ischemia or ischemic heart disease including reperfusion injury. Peptide P may be formulated for administration in an aqueous based liquid such as phosphate buffered saline to form an emulsion, or it may be formulated in an organic liquid such as cyclodextrin or dimethylsulfoxide to form a solution. The peptide-P active ingredient should be present in an effective amount of about 0.001 wt. % up to 25.0 wt. % in such compositions. The solution or emulsion may be administered by any route, but it is preferably administered parenterally such as by intravenous, intramuscular, intradermal or intraperitoneal injections.

A preferred Peptide P dose is in the range of about 0.5 mg/kg body weight of the mammal to about 20 mg/kg body weight of the mammal, or alternatively lower doses of about 1 mg/kg body weight of the mammal to about 1000 mg/kg body weight of the mammal. The time of administration of a single dose of Peptide P is preferably up to about four hours after onset of an ischemic episode. However, Peptide P may be administered concurrently with the onset of a ischemic episode or even prior to onset of ischemia and still produce a therapeutic effect.

Efficacy of Peptide P treatment may be evaluated using noninvasive clinical imaging methods such as magnetic resonance imaging (MRI) of the affected region to determine the size of the damaged area. In cerebral ischemia, it is also possible to assess neurologic deficit by performance on behavioral tests such as cognitive recognition or memory function such as the National Institutes of Health (NIH) stroke scale.

While the specific mechanism of Peptide P action on ischemia is unknown, Peptide P exhibits a specific and reproducible effect on decreasing neurological deficit and cerebral infarct volume. This invention will be further appreciated in light of the following example.

The following example is presented to illustrate the invention but the invention is not considered to be limited thereto.

EXAMPLE

A murine model of ischemia/reperfusion injury was used to evaluate the effects of Peptide P on cerebral blood flow, behavioral changes and ischemia infarct volume.

Induction of Ischemia

Ischemia was induced by transient occlusion of the external carotid artery (ECA). Male ICR mice weighing about 30–35 g were anesthetized with an intraperitoneal (i.p.) injection of chloral hydrate (350 mg/kg of body weight) and xylazine (4 mg/kg of body weight). Rectal temperatures were maintained at 37±0.5° C. with a heating pad and incubator. The left femoral artery was cannulated with a PE-10 catheter for measurement of arterial blood pressure, pO2, pCO2 and pH.

A midline incision was made in the skin of the neck and the left common carotid artery (LCCA) was exposed. The ECA, superior thyroid artery (STA) and occipital artery (OA) were isolated. The STA and OA were electrocoagulated using a cautery probe (Baster Hi Temp Cautery, Baxter Healthcare Corp.) and divided. The base of the ECA was secured with a microsurgical clip, then the distal end of the ECA was ligated with a 6-0 nylon suture and the ECA was cut. A blunted 5-0 blue monofilament nylon suture was placed in the end of the ECA, the surgical clip was removed, then the blunted suture was advanced into the ECA until resistance was detected. The blunted suture was then tightened to prevent both slipping of the internal suture and bleeding. The suture was trimmed and the incision was sealed by suturing the skin. The suture remained in place for varying lengths of time up to 24 h. At the desired time, reperfusion of the brain (restoration of blood flow to the brain) was accomplished by retreating the suture from the ECA.

Mean arterial blood pressure (MABP), pO2, pCO2 and pH were measured before occlusion, 10 min after occlusion and 30 min after reperfusion. Cerebral blood flow was monitored by laser-Doppler flowmetry with a fiber optic probe placed 2 mm posterior and 6 mm lateral to the bregma on the ipsilateral hemisphere of the brain.

Treatment

The test compound was Peptide P (Tyr-D-Ala-Phe-Ala-Asp-Val-Ala-Ser-Thr-Ile-Gly-Asp-Phe-Phe-His-Ser-Ile-NH2). For analysis of the test compound, a solution of the test compound in saline or 1% cyclodextrin was prepared. The test compound in solution was administered by I.V. injection at multiple doses prior to or up to 4 hours following ischemic injury.

Control animals (n=5) received I.V. injections of saline or 1% cyclodextrin. Peptide P treated animals (n=6) received 4 mg/kg of Peptide P 1 hour following middle cerebral antery occlusion (MCAO). At time O, animals were subjected to 1 hour focal middle cerebral arterial occlusion (MCAO) ischemia and 24 hour of reperfusion. Cerebral blood was assessed by laser-Doppler flowmetry with a fiber optic probe prior to ischemia and at 0.5 hour, 1 hour and 2 hours post ischemia. Ischemic volume was measured and animals were assessed for behavior changes using a numerical ranking from 0 to 3 according to the following criteria: 0=no observable deficits (normal); 1=failure to extend right forepaw upon lifting by the tail (mild); 2=circling to the contralateral side (moderate); and 3=leaning to the contralateral side at rest or no spontaneous motor activity (severe).

Evaluation of Treatment

Brain infarct volume was measured after 1 hour of ischemia and again at 24 hours after reperfusion. At the desired endpoint, the animal was euthanized. The brain was immediately removed and placed into a mouse brain matrix (ASI, Warren, MI) and 2 mm sections were made. Brain sections were stained with 2% 2,3,5-triphenyltetrazolium chloride (TTC). Infarct size was determined according to the formula:

$$(\text{Contralateral volume} - \text{ipsilateral undamaged volume}) \times 100 / \text{Contralateral volume}$$

to eliminate the effects of edema. Quantitation of contralateral and ipsilateral volumes was determined by image analysis using a Scion Image (NIH Image Version 1.59) modified by Scion Corp. and Adobe Photoshop 2.0.1.

Statistical analysis of the volume analysis results was performed using the Student's t-test or analysis of variance (ANOVA) followed by the Bonferroni test. Statistical significance was assigned to comparisons of sections from control versus Peptide P treated animals with $p<0.006$. Data were expressed as mean±standard error of the mean (SEM)

Prior to Peptide P treatment, there were no significant differences in MABP, pO2, pCO2, pH or rectal temperature between control animals and deltorphin-treated animals. Upon induction of ischemia by middle cerebral arterial occlusion, both control and Peptide P- treated animals had a 25% reduction in cerebral blood flow which was sustained for 1 hour during the ischemia. After cessation of ischemia, cerebral blood flow returned to baseline levels within 0.5 hour. Post ischemia, there were no significant differences in MABP, pO2, pCO2, pH or rectal temperature between control animals and deltophin-treated animals. There was, however, a significant (<0.05) decrease in neurological deficits from Peptide P treated animals (0.44±11) versus control animals (1.55±0.19). Additionally, infarct volume was also significantly reduced by 59% in Peptide P- treated animals (24±4.8 mm3) compared to control animals (58±7.2 mm3) after 24 h of reperfusion, see FIG. 1, Table 1 & 2.

TABLE 1

| Mouse strain/C57 | Peptide-P (Pep-P) | | | | | | | |
|---|---|---|---|---|---|---|---|---|
| No. | Pep-P 1 | Pep-P 2 | Pep-P 3 | Pep-P 4 | Pep-P 5 | Pep-P 6 | Total | Average |
| Sex | M | M | M | M | M | M | | |
| Ischemia Time | 1 hr | 1 hr | 1 hr | 1 hr | 1 hr | 1 hr | | |
| Reperfusion Time | 24 hr | 24 hr | 24 hr | 24 hr | 24 hr | 24 hr | | |
| Cross Section Area 1 | 10.43 | 9.53 | 10.74 | 13.46 | 11.00 | 11.71 | | |
| Cross Section Area 2 | 17.91 | 16.64 | 17.44 | 19.06 | 18.11 | 18.8 | | |

TABLE 1-continued

Peptide-P (Pep-P)

| Mouse strain/C57 No. Sex | Pep-P 1 M | Pep-P 2 M | Pep-P 3 M | Pep-P 4 M | Pep-P 5 M | Pep-P 6 M | Total | Average |
|---|---|---|---|---|---|---|---|---|
| Cross Section Area 3 | 19.77 | 19.62 | 19.46 | 20.7 | 21.19 | 21.3 | | |
| Cross Section Area 4 | 20.43 | 18.93 | 19.26 | 19.73 | 20.85 | 20.73 | | |
| Total Cross Section Area | 68.54 | 64.72 | 66.9 | 72.95 | 71.15 | 72.54 | 416.8 | 68.77 ± 1.4% |
| Damaged Cross Section Area 1 | 3.69 | 0 | 1.42 | 1.89 | 0 | 0.27 | | |
| Damaged Cross Section Area 2 | 5.66 | 0.32 | 1.38 | 3.27 | 4.59 | 1.8 | | |
| Damaged Cross Section Area 3 | 6.47 | 1.12 | 2.63 | 7.23 | 2.22 | 5.15 | | |
| Damaged Cross Section Area 4 | 1.84 | 1.11 | 3.06 | 5.54 | 6.11 | 4.46 | | |
| Damaged Cross Section Area | 17.66 | 2.55 | 8.49 | 17.93 | 12.92 | 11.68 | 71.23 | 11.87 ± 2.4% |
| Damaged % | 25.77 | 3.94 | 12.69 | 24.58 | 18.16 | 16.10 | 101.24 | 16.87 ± 3.3% |
| Corrected Volume | 35.32 | 5.10 | 16.98 | 35.86 | 25.84 | 23.36 | 142.46 | 23.74 ± 4.8% mm$^3$ |

Corrected Volume (mm$^3$) = Damaged Cross Section Area X 2 mm section
After 1 hr ischemia mice were injected with 100 µl Peptide-P (4 mg/Kg)

TABLE 2

Saline

| Mouse strain/C57 No. Sex | Saline 1 M | Saline 2 M | Saline 3 M | Saline 4 M | Saline 5 M | Total | Average |
|---|---|---|---|---|---|---|---|
| Ischemia Time | 1 hr | 1 hr | 1 hr | 1 hr | 1 hr | | |
| Reperfusion Time | 24 hr | 24 hr | 24 hr | 24 hr | 24 hr | | |
| Cross Section Area 1 | 14.81 | 14.65 | 12.55 | 13.18 | 15.35 | | |
| Cross Section Area 2 | 22.52 | 22.39 | 19.52 | 20.68 | 22.08 | | |
| Cross Section Area 3 | 25.24 | 25.45 | 21.84 | 23.51 | 24.77 | | |
| Cross Section Area 4 | 24.51 | 24.05 | 21.54 | 24.98 | 23.81 | | |
| Total Cross Section Area | 87.08 | 86.54 | 75.45 | 82.35 | 86.01 | 417.43 | 83.49 ± 2.2% |
| Damaged Cross Section Area 1 | 6.58 | 4.49 | 1.77 | 1.02 | 4.83 | | |
| Damaged Cross Section Area 2 | 9.7 | 6.86 | 2.42 | 2.21 | 8.81 | | |
| Damaged Cross Section Area 3 | 11.86 | 10.7 | 7.65 | 5.79 | 9.52 | | |
| Damaged Cross Section Area 4 | 10.02 | 12.22 | 9.03 | 11.21 | 8.26 | | |
| Damaged Cross Section Area | 38.16 | 34.27 | 20.87 | 20.23 | 31.42 | 144.95 | 28.99 ± 3.6% |
| Damaged % | 43.82 | 39.60 | 27.66 | 24.57 | 36.53 | 172.18 | 34.45 ± 3.6% |
| Corrected Volume | 76.32 | 68.54 | 41.74 | 40.46 | 62.84 | 289.9 | 57.98 ± 7.2% mm$^3$ |

Corrected Volume (mm$^3$) = Damaged Cross Section Area X 2 mm section
After 1 hr ischemia mice were injected with 100 µl physiological saline Identification of a novel seventeen amino acid Peptide, Peptide P and a method for treating cerebral or spinal cord ischemia or ischemic heart disease including reperfusion injury by Peptide P administration is thus disclosed. Peptide P, SEQ ID NO:1 is formulated for biocompatible administration in a preferred dose in the range of about 0.5–20 mg/kg, or alternatively 1–1000 mg/kg body weight of the animal. The Peptide P dose may be administered up to four hours after the onset of an ischemic attack. Alternatively, the Peptide P dose may be administered prophylactically in patients at risk for an ischemic attack such as, for example, prior to surgery. Peptide P administration reduces the effect of an ischemic event.

It should be understood that the embodiments of the present invention shown and described in the specification are only preferred embodiments of the inventors who are skilled in the art and thus are not limiting in any way. Therefore various changes, modifications or alterations to these embodiments may be made or restored to without departing from the spirit of the invention and the scope of the following claims.

What is claimed is:

1. Peptide P comprising the amino acid sequence, Tyr-D-Ala-Phe-Ala-Asp-Val-Ala-Ser-Thr-Ile-Gly-Asp-Phe-Phe-His-Ser-Ile-NH2.

2. A pharmaceutical composition comprising a pharmaceutically effective amount of Peptide P having the amino acid sequence, Tyr-D-Ala-Phe-Ala-Asp-Val-Ala-Ser-Thr-Ile-Gly-Asp-Phe-Phe-His-Ser-Ile-NH2 and a pharmaceutically acceptable carrier.

* * * * *